United States Patent

Rapko

[11] 4,118,568
[45] Oct. 3, 1978

[54] N-ACETYL DIGLYCOLIMIDE

[75] Inventor: John N. Rapko, St. Louis, Mo.

[73] Assignee: Monsanto Company, St. Louis, Mo.

[21] Appl. No.: 830,250

[22] Filed: Sep. 2, 1977

[51] Int. Cl.² .............................................. C07D 265/32
[52] U.S. Cl. ..................................... 544/173; 252/95; 252/99; 252/102
[58] Field of Search ......................................... 544/173

[56] References Cited
U.S. PATENT DOCUMENTS

| 3,309,365 | 3/1967 | Merijan et al. | 544/173 |
| 3,785,984 | 1/1974 | Berg et al. | 252/99 |

Primary Examiner—Henry R. Jiles
Assistant Examiner—R. W. Ramsuer
Attorney, Agent, or Firm—S. M. Tarter; E. P. Grattan; F. D. Shearin

[57] ABSTRACT

The novel compound:

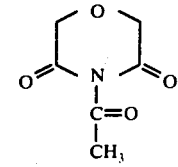

is disclosed, together with its use as an activator for hydrogen peroxide bleaches, or bleaches which yield hydrogen peroxide. Activation proceeds quickly at relatively low temperatures. Activator, bleach and washing compounds can all be used together.

1 Claim, No Drawings

N-ACETYL DIGLYCOLIMIDE

This application relates to a compound found to be useful in the low-temperature activation of peroxide bleaches, and per-compound bleaches which yield hydrogen peroxide in water. Such bleaches are used, with and without washing agents, in bleaching fabrics. In such use, however, these bleaches are relatively ineffective at temperatures below about 80° C.; and, hence, their use is limited to systems which can produce such high temperatures, and to fabrics which can be safely exposed to such high temperatures.

BACKGROUND OF THE INVENTION

Some activating materials have been proposed which, when used in combination with the above-mentioned bleaches, lower the temperature at which the bleaches are effective. U.S. Pat. No. 3,185,649, for example, teaches the use of sodium p-acetylbenzenesulfonate as an activator for such bleaches. U.S. Pat. No. 3,785,984, teaches the use, among other compounds, of N,N,N',N'-tetraacetylethylenediamine as a bleach activator. The mechanism of activation in each case is the formation of organic peracids when combined with the bleach in aqueous solution. The peracids are very effective bleaching agents at temperatures below 60° C., down to as low as about 20 C.

SUMMARY OF THE INVENTION

It is an object of this invention to provide a relatively inexpensive activator for bleaches which are hydrogen peroxide or percompounds which yield hydrogen peroxide in aqueous solutions. It is another object to provide an activator for hydrogen peroxide bleach which will activate such a bleach quickly at relatively low temperatures. These and other objects are accomplished by the use of a novel compound of the formula:

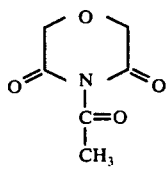

DESCRIPTION OF THE PREFERRED EMBODIMENTS

The compound of the invention can be defined as N-acetyldiglycolimide, and will be referred to herein as NADI. In evaluating the effectiveness of NADI as a bleach activator, its performance was compared with that of sodium p-acetylbenzenesulfonate (hereinafter referred to as "SABS") and N,N,N',N'-tetraacetylethylenediamine (hereinafter referred to as "TAED").

Synthesis of NADI was performed according to the following procedure:

Into a 250 ml. flask equipped with a magnetic stirrer, reflux condenser and gas inlet tube was charged 11.5 grams (0.1 mole) of diglycolimide and 0.1 gram of fused sodium acetate. Also charged was 100 ml. of acetone. The contents of the flask were heated under agitation to 45° C. An excess of ketene was bubbled into the flask, with no exotherm noted. All solid materials were in solution after about 10 minutes, when the reaction mixture gradually turned yellow, then orange. After 17 minutes, ketene addition was stopped. The reaction mixture was then transferred to a 250 ml. erlenmeyer flask and treated with a decolorizing charcoal. The mixture was filtered hot, then rotoevaporated to remove the acetone. A yellow oily material remained, which was added to 150 ml. of ethanol, solidifying at once. The solid mass was ground under ethanol, filtered, and dried under vacuum at room temperature. A total of 11.8 grams of product was recovered, which has a melting point of 79°-81° C.

The product was calculated to have the empirical formula: $C_6H_7NO_4$. Analysis is set forth in Table I below:

TABLE I

|  | Theory, % | Found, % |
|---|---|---|
| Carbon | 45.86 | 45.91 |
| Hydrogen | 4.49 | 4.46 |
| Nitrogen | 8.91 | 8.96 |
| Oxygen | 40.72 | 40.67* |

*by difference $^1$H NMR results in $_6$ acetone showed a singlet at 2.5 ppm (3 protons) and a singlet at 4.5 ppm (4 protons). These results are consistent with the proposed structural formula for NADI, indicating the three hydrogen atoms on the $CH_3$ group of the acetyl radical, and the four hydrogen atoms contained in the two $CH_2$ groups in the diglycolimide ring.

In a preliminary screening, NADI was compared with SABS and TAED using a titration which is described in U.S. Pat. No. 3,785,984, in column 6 at lines 65-75, continued in column 7 at lines 1-9. The titration is set forth as follows:

"The activation value (=titre) for the activators is determined in the following way: Solutions which contain 0.615 gm./liter of $NaBO_2$—$H_2O_2$—$3H_2O$ (4 mmol/liter) and 2.5 gm./liter of $Na_4P_2O_7$—$10H_2O$, are heated to 60° C., and then are mixed with 4 mmol/liter of activator and maintained at the said temperature for 5 minutes with stirring. Then 100 ml. of this liquid is added to a mixture of 250 gm. of ice and 15 ml. of glacial acetic acid and titrated immediately after addition of 0.35 gm. of potassium iodide with 0.1 N sodium thiosulfate solution, using starch as indicator. Under the given experimental conditions, for a 100% activation of the peroxide used, 8.0 ml. of thiosulfate solution are consumed, the titre is 8.0. This maximum value is, of course, seldom attained. Good activators have a titre of at least 4.5, preferably from 5 to 7. Useful results are often obtained with activators having a titre of at least 3.0."

By means of the foregoing procedure "Titre" values were obtained as set forth in Table II below:

TABLE II

| Activator | Titre |
|---|---|
| SABS | 3.03* |
| TAED | 5.07* |
| NADI | 1.0 |

*average of three runs.

The results for NADI in Table I would seem to indicate that its value as an activator for sodium perborate bleach is minimal. However, further testing was performed to measure the relative oxidation potentials obtained by SABS, TAED and NADI in combination with aqueous solutions of sodium perborate. The test procedure followed is basically described in U.S. Pat. No. 3,640,876, in column 6 at lines 43-56, and is here repeated:

"A standard procedure was followed in evaluating each of these compositions. Thus, a measured amount of the composition being tested was introduced into 200 ml. of a buffer solution of 0.01 M $Na_2B_2O_4$ in an amount sufficient to provide a concentration of 1 gm. perborate per liter. The temperature of the solution was maintained at about 50° C. throughout the test period. The electrochemical potential shift of the solution formed by the compositions being tested was measured using platinum-saturated Calomel electrodes. In addition, a glass Calomel electrode was provided in the solution and connected to the recording potentiometer so that changes in pH could be followed. The change in EMF for each composition was measured in this manner for about 15 minutes."

A stock buffer solution of 1% sodium tripolyphosphate was prepared by dissolving 10 grams of STP into water to form a liter of the solution. A recording potentiograph was then set up for a range of 0 to +750 millivolts. A jacketed beaker was placed on a magnetic stirrer, with the stirrer bar and a thermometer in the beaker. Water at 50° C. was circulated through the jacket. Into the beaker was charged 200 ml. of the 1% STP solution, and the electrodes connected to the potentiograph were placed in the beaker, immersed in the STP solution.

While the temperature of the STP solution was warming from room temperature to 50° C., 0.2 gram amounts of sodium perborate and of the activator to be tested were weighed out carefully (±0.05 g). When the STP solution reached 50° C., both the perborate and activator were added simultaneously to the beaker, and the potentiograph recorder was started. Millivolt changes were recorded at 5, 15 and 30 minutes. Samples of SABS, TAED and NADI were each tested in the above procedure, and the results are noted in Table III below:

TABLE III

| Activator | Maximum Δ Mv. |
|---|---|
| SABS | + 80 |
| TAED | +320 |
| NADI | + 80 |

The results in Table III above indicate that SABS and NADI give roughly the same performance, and that TAED is considerably superior. In theory, an increase in oxidation potential will be shown if the activator forms peracid with the perborate. A direct comparison can be made among activators, based on the time rate of potential increase shown. The maximum value of +80 for SABS and NADI was reached in less than 30 seconds, while the TAED required 11 minutes to reach its maximum value of +320, and did not rise above +80 until about three minutes into the test.

Here, NADI appears to be as good as SABS, and reaches its maximum potential considerably faster than does TAED. Since the test was performed at 50° C., it is not particularly indicative of the expected behavior of these activators at 25° C.

Since the results of the "Titre" evaluation and of the oxidation potential measurements both are rather inconclusive as to the suitability of NADI as a low-temperature bleach activator, it was decided to evaluate NADI further, in a test designed to better show behavior of the activator at room temperature.

A "double-titration" test was set up, wherein, briefly stated, samples of activator, together with an excess of perborate bleach were titrated at 25° C. first with sodium thiosulfate; then with ceric sulfate. The former titration will measure amounts of peracid plus peroxide present; that is, the total active oxygen. The latter titration measures the amount of $H_2O_2$ present. Thus, by difference, the amount of peracid present can be found.

The ceric sulfate titration was performed as follows: A test solution was prepared by accurately weighing and transferring into a 500 ml. volumetric flask 7.7 grams of sodium perborate and 5.0 grams of sodium tripolyphosphate. Deionized water was added to the mark on the flask. The solution was brought to 25° C.

Six grams of NADI were carefully weighed and added to the flask with stirring. Samples of the activated solutions were then taken off and titrated at 5, 10, 15 and 30-minute intervals.

A twenty-five ml. aliquot of the test solution was withdrawn and transferred to a 500 ml. iodine flask which contained 200 g. of ice and 20 ml. of concentrated sulfuric acid. Four drops of 0.025 M Ferroin indicator were added, and the solution was immediately titrated with 0.1N ceric sulfate to the disappearance of the salmon color of the indicator.

Similarly, SABS and TAED were evaluated, as was NADI, except that only 3.0 grams of TAED were used, since it possesses an effective acid functionality which is at least twice that of SABS and NADI.

For the sodium thiosulfate titration, the same test solutions were used as in the ceric sulfate titrations, with five, ten, fifteen and thirty minute samples. For the sodium thiosulfate titration, each 25 ml. aliquot was added at the proper time interval to 500 ml. iodine flasks containing 20 ml. of concentrated sulfuric acid, 200 ml. of deionized water, and 3.0 grams of potassium iodide. Five ml. of starch indicator solution was added, and the mixture was titrated to a clear end point with 0.1N sodium thiosulfate.

The titrations showed the decomposition of both $H_2O_2$ and peracid, with some formation of peracid from the interaction of the activator and bleach.

The values for ml. of both titrants were multiplied by 0.1, the normality of each solution, to give the number of milliequivalents present of $H_2O_2$ and of total active oxygen for each activator at each time interval. These figures are set out for NADI in Table IV below:

TABLE IV

| | NADI Activation | | |
|---|---|---|---|
| Time, min. | Total Active Oxygen | $H_2O_2$ | Peracid (by difference) |
| 5 | 4.45 | 3.08 | 1.37 |
| 10 | 4.27 | 2.92 | 1.35 |
| 15 | 4.18 | 2.85 | 1.33 |
| 30 | 4.12 | 2.76 | 1.36 |

The data in Table IV show that using NADI, the peracid level rose sharply in less than five minutes to a value of 1.37 meq., and maintained this level, while the values for $H_2O_2$ and total active oxygen decayed gradually.

In Table V below, the similar data are set forth for SABS:

TABLE V

SABS Activation

| Time, min. | Total Active Oxygen | H₂O₂ | Peracid (by difference) |
|---|---|---|---|
| 5 | 4.92 | 2.52 | 2.40 |
| 10 | 4.91 | 2.52 | 2.39 |
| 15 | 4.86 | 2.49 | 2.37 |
| 30 | 4.76 | 2.39 | 2.37 |

Table V data indicate that with SABS the peracid level rose even more sharply than with NADI, to a level of about 2.4, and this level was sustained through the test duration.

In Table VI below, the similar data are set forth for TAED:

TABLE VI

TAED Activation

| Time, min | Total Active Oxygen | H₂O₂ | Peracid (by difference) |
|---|---|---|---|
| 5 | 4.98 | 4.07 | 0.91 |
| 10 | 5.00 | 3.83 | 1.17 |
| 15 | 4.97 | 3.62 | 1.35 |
| 30 | 4.76 | 3.07 | 1.69 |

Table VI data show that with TAED as an activator, the level of peracid is lower at five and at ten minutes than either of the other activators, and not until 15 minutes is the peracid level equal to that obtained with NADI. The peracid level continued to rise with time, as the total active oxygen level gradually decreased.

It can be seen, from a comparison of the three activators tested, that although TAED was clearly more effective at the higher temperatures used in the "Titre" test and in the oxidative potential test, it did not compare as favorably at 25° C. with SABS and NADI.

Since the intended use of the activator of the invention is at relatively lower temperatures, its utility at, for example, 25° C. is clearly shown. Also, while TAED does eventually rise to the performance of NADI (after 15 minutes), a shorter process cycle in bleaching would find TAED significantly less efficient at temperatures on the order of 25° C.

The compound of the invention is used to advantage in combination with $H_2O_2$ or a peroxide compound which forms $H_2O_2$ in aqueous solution. The compound can be used in a ratio of from 0.1 to 10 moles per mole of $H_2O_2$ or peroxide compound.

The compound of the invention can be used in aqueous bleaching operations in combination with peroxide bleaches only, or in aqueous solutions which also contain one or more washing agents and auxiliary materials, such as alkali metal builder salts, soaps, organic sequestering agents, corrosion inhibitors, optical brighteners, anionic, nonionic, amphoteric and ampholytic surfactants, enzymes, soil suspension agents, alkali metal silicates, textile softeners, and foam stabilizers.

Although the invention has been illustrated by typical examples, it is not limited thereto. Changes and modifications of the examples of the invention herein chosen for purposes of disclosure can be made which do not constitute departure from the spirit and scope of the invention.

The embodiments of the invention in which an exclusive property or privilege is claimed are defined as follows:

1. The compound of the formula:

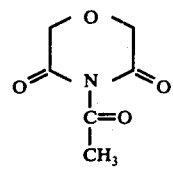

* * * * *